United States Patent
Machida et al.

(10) Patent No.: US 7,390,320 B2
(45) Date of Patent: Jun. 24, 2008

(54) AUTOMATIC URINE DISPOSAL DEVICE AND URINE RECEPTACLE USED THEREFOR

(75) Inventors: Shigeru Machida, Iwama (JP); Junichi Kobayashi, Ushiku (JP); Yuji Yoshitomi, Chiyoda (JP); Akiomi Kouno, Tomobe (JP); Ryousuke Miyagawa, Kasukabe (JP); Ichiro Wada, Toyohama (JP); Miou Suzuki, Toyohama (JP)

(73) Assignees: Hitachi, Ltd., Tokyo (JP); Uni-Charm Corporation, Shikokuchuo-Shi (JP)

( * ) Notice: Subject to any disclaimer, the term of this patent is extended or adjusted under 35 U.S.C. 154(b) by 16 days.

(21) Appl. No.: 10/912,085

(22) Filed: Aug. 6, 2004

(65) Prior Publication Data

US 2005/0033248 A1 Feb. 10, 2005

(30) Foreign Application Priority Data

Aug. 6, 2003 (JP) .............................. 2003-206340

(51) Int. Cl.
*A61M 1/00* (2006.01)
*A61F 5/44* (2006.01)
*A47K 11/00* (2006.01)
(52) U.S. Cl. .................. 604/320; 604/540; 604/327; 604/355; 4/144.1
(58) Field of Classification Search .......... 604/540, 604/544, 313, 317–357; 4/144.1, 144.2, 4/144.3, 144.4
See application file for complete search history.

(56) References Cited

U.S. PATENT DOCUMENTS

| 4,631,061 | A |   | 12/1986 | Martin |
|-----------|---|---|---------|--------|
| 4,747,166 | A | * | 5/1988  | Kuntz .......................... 4/144.1 |
| 5,911,222 | A |   | 6/1999  | Lawrence |
| 5,916,507 | A | * | 6/1999  | Dabi et al. .................. 264/113 |
| 5,957,909 | A | * | 9/1999  | Hammons et al. ........... 604/387 |

(Continued)

FOREIGN PATENT DOCUMENTS

EP 0483592 5/1992

(Continued)

OTHER PUBLICATIONS

Ethafoam and Other Polyethylene Foams in Conservation, Scott Williams, 1998, http://palimpsest.stanford.edu/byauth/williams/foam.html.*

(Continued)

*Primary Examiner*—Tatyana Zalukaeva
*Assistant Examiner*—Michael G Bogart
(74) *Attorney, Agent, or Firm*—Antonelli, Terry, Stout & Kraus, LLP.

(57) ABSTRACT

An automatic urine disposal device has a urine collecting pad, vacuum pump, and urine tank. In the urine collecting pad, the top sheet comes in contact with the wearer's skin, the hydrophilic sheet is disposed on the bottom of the top sheet, and the urine absorbent sheet is disposed at the bottom. When discharged urine flows in the top sheet, the hydrophilic sheet widely diffuses urine to saturate its entire surface and then becomes non-breathable. As the vacuum pump vacuums the air from the urine tank, urine is directed from a urine drainage port of the urine collecting pad via a urine drainage tube to the urine tank which is a sealed container.

15 Claims, 5 Drawing Sheets

U.S. PATENT DOCUMENTS

| | | | |
|---|---|---|---|
| 6,706,027 B2 * | 3/2004 | Harvie | 604/347 |
| 2001/0037097 A1 | 11/2001 | Cheng | |
| 2004/0236292 A1 * | 11/2004 | Tazoe et al. | 604/317 |

FOREIGN PATENT DOCUMENTS

| | | |
|---|---|---|
| GB | 2244653 | 12/1991 |
| JP | 7-171182 | 7/1995 |
| JP | 8-191852 | 7/1996 |
| WO | 9309736 | 5/1993 |

OTHER PUBLICATIONS

U.S. Appl. No. 10/796,025, (2004), entitled "Automatic Urine Disposal Device And Urine Receptacle Used Therefor".

H. Shimizu, et al., "Study on Voiding Diturbance in Elderly Males", Urology Bulletin, vol. 33, No. 4, (1987).

* cited by examiner

AUTOMATIC URINE DISPOSAL DEVICE AND URINE RECEPTACLE USED THEREFOR

The present application claims priority from Japanese application JP2003-206340 filed on Aug. 6, 2003, the content of which is hereby incorporated by reference into this application.

BACKGROUND OF THE INVENTION

The present invention relates to an automatic urine disposal device worn by the bedridden elderly, hospitalized patients, physically disabled people, and others who are unable to voluntarily control the bladder or to clean up urine on their own and also relates to a urine receptacle or a collecting pad used therefor.

Because of age, physical disability, hospitalization due to injury or illness, or other physical conditions, people sometimes become unable to voluntarily control the bladder or clean up urine on their own. In those situations, generally, a catheter is directly inserted into the bladder to discharge urine or paper diaper is used.

When a catheter is directly inserted into the bladder, the wearer feels great discomfort and there is also the probability of injuring the urethra or bladder or the occurrence of an infection. Thus, expertise as well as special sterilized utensils is required.

When a paper diaper is worn for a prolonged period of time, urine may leak, the wearer can become uncomfortable, get stuffy, or skin troubles such as rashes may occur. To avoid this, the paper diaper must be frequently changed, which will impose considerable physical and mental burdens on both the wearer and the caretaker. Imposed on a daily basis, those physical and mental burdens become a big concern and a significant economical burden as well.

To avoid those problems, a method has been presented in which urine that has been absorbed by a urine absorbent material of a urine collecting pad is discharged by means of a vacuum pump and drawn into a urine tank. The vacuum pump suctions air from a sealed urine tank and due to the difference between the tank's pressure and the atmospheric pressure, urine absorbed in the urine collecting pad is drained into the urine tank. Automatic urine disposal devices of such configuration have been disclosed in Japanese Application Patent Laid-Open Publication No. Hei 07-171182 and No. Hei 08-191852.

In the conventional urine disposal devices, urine is drained while the urine collecting pad abuts up against the wearer's urinating part, that is, the urine collecting pad's urine absorbent material is being exposed to atmospheric air, and therefore, the percentage of urine collection from the urine collecting pad (urine absorbent material) is low. For this reason, the amount of urine which remains in the urine collecting pad (urine absorbent material) is large, which makes the wearer feel uncomfortable. To reduce the amount of urine which remains in the urine collecting pad, the capacity of the vacuum pump must be increased. Accordingly, it becomes necessary to increase the size and volume of the urine disposal device. Thus, in fact, the conventional urine disposal device has no practical use as a portable urine disposal device. As stated above, in the conventional techniques, there are problems in that the amount of urine which remains in the urine collecting pad is large and to reduce the amount, the urine disposal device must be large and heavy.

BRIEF SUMMARY OF THE INVENTION

The objective of the present invention is to provide a compact and lightweight automatic urine disposal device which increases the percentage of urine collection by the urine collecting pad and also to provide a urine collecting pad used therefor.

To achieve the aforementioned objective, the present invention is designed such that it uses a urine collecting pad in which a hydrophilic sheet is disposed on the surface of the urine absorbent sheet, and when discharged urine flows into the hydrophilic sheet from the top sheet, the hydrophilic sheet widely diffuses urine to saturate its entire surface thereby creating a non-breathable condition, and urine is then directed through the urine drainage port of the urine collecting pad via a urine drainage tube to a sealed urine tank by the operation of a vacuum pump.

In other words, in the present invention, a hydrophilic sheet which becomes non-breathable by absorbing urine is disposed on the surface of the urine absorbent sheet contained in the liquid-impermeable, non-breathable outer sheet, and the urine absorbent sheet is kept air-tight (sealed) by the outer sheet and the hydrophilic sheet when urine is discharged, and a vacuum pump creates negative pressure in the urine drainage port created on the outer sheet, thereby draining urine and directing it to the urine tank via a urine drainage tube.

Herein, a hydrophilic sheet in this specification means a sheet which is breathable, liquid-permeable, has saturation property, and widely diffuses urine to saturate the entire surface by surface tension. In the urine collecting pad used for the present invention, the urine absorbent sheet is kept airtight by the outer sheet and the hydrophilic sheet when urine is discharged. Therefore, the percentage of urine collection from the urine collecting pad by the operation of the vacuum pump increases and the amount of urine which remains in the urine collecting pad is reduced. With the increase in the percentage of urine collection, a small-capacity vacuum pump with a low suction force can drain urine. Therefore, it is possible to drain urine from the urine collecting pad without discomfort to the wearer, and the device can be compact and lightweight.

DETAILED DESCRIPTION OF THE INVENTION

Figure 1:
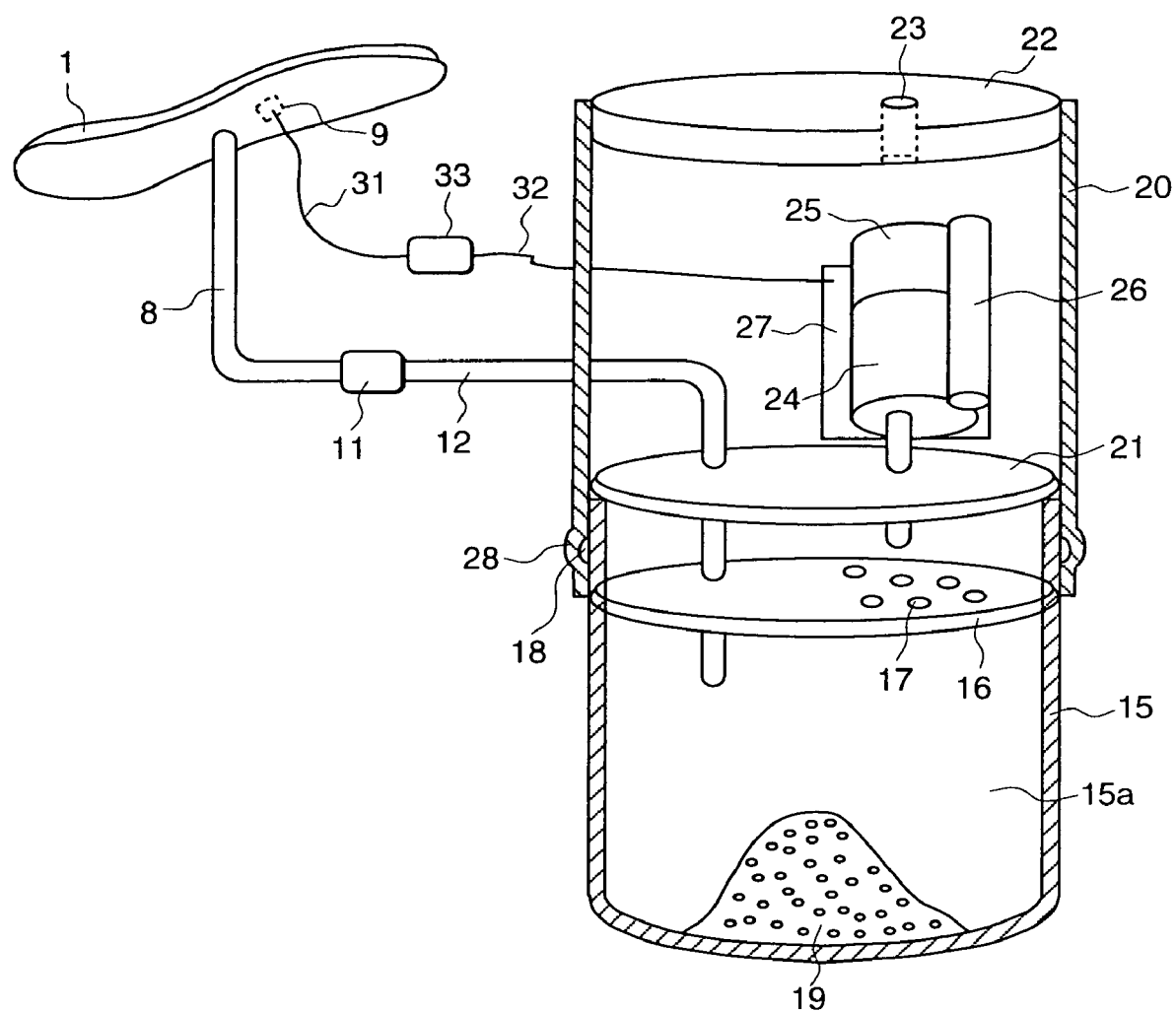
FIG. 1 is an elevation partly in section of an embodiment of an automatic urine disposal device according to the present invention.
Figure 2:
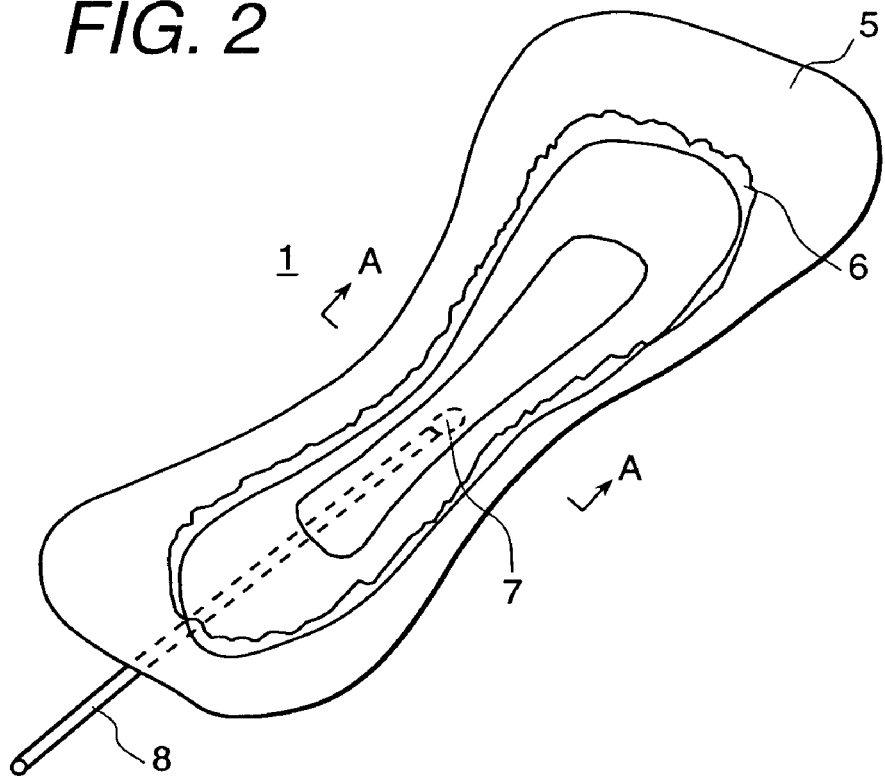
FIGS. 2 through 5 are a top view, bottom view, exploded perspective view, and a cross-sectional view taken along A-A line in FIG. 2, respectively, of the urine collecting pad installed in the automatic urine disposal device shown in FIG. 1.
Figure 3:
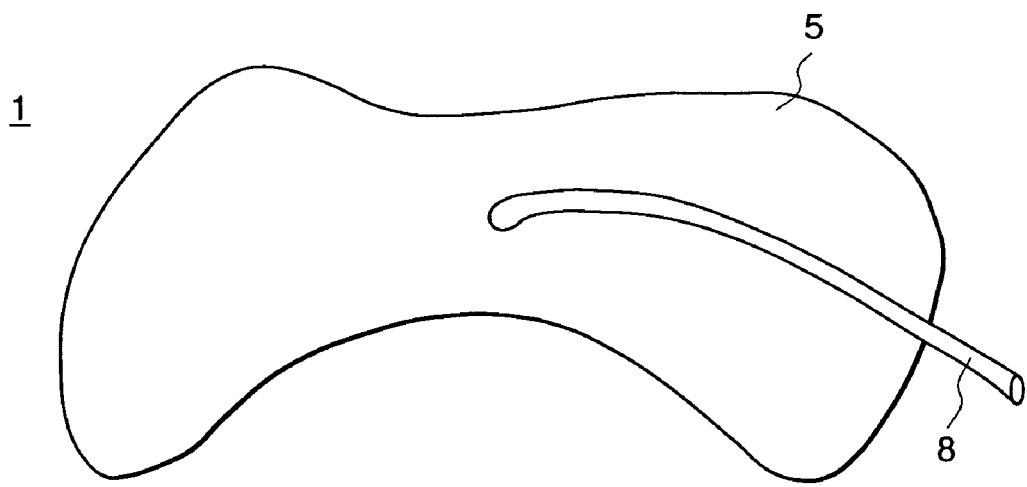
Figure 4:
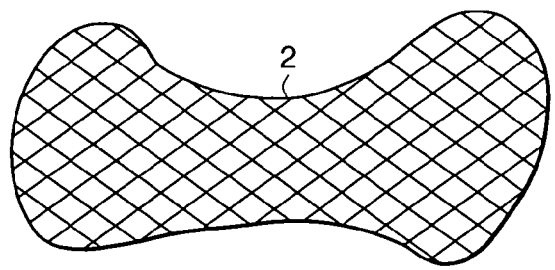
Figure 4:
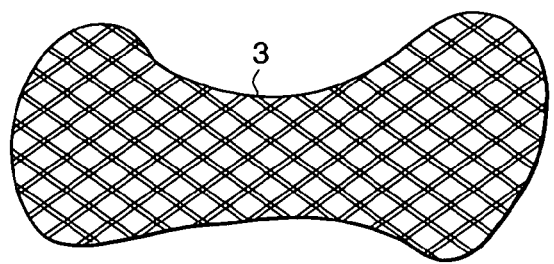
Figure 4:
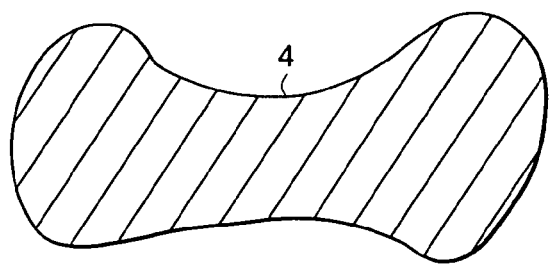
Figure 4:
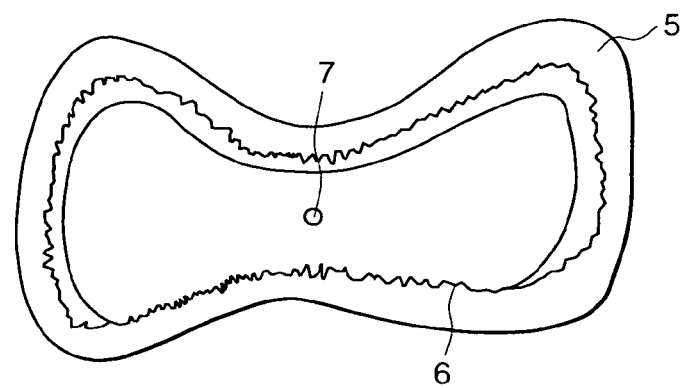
Figure 5:
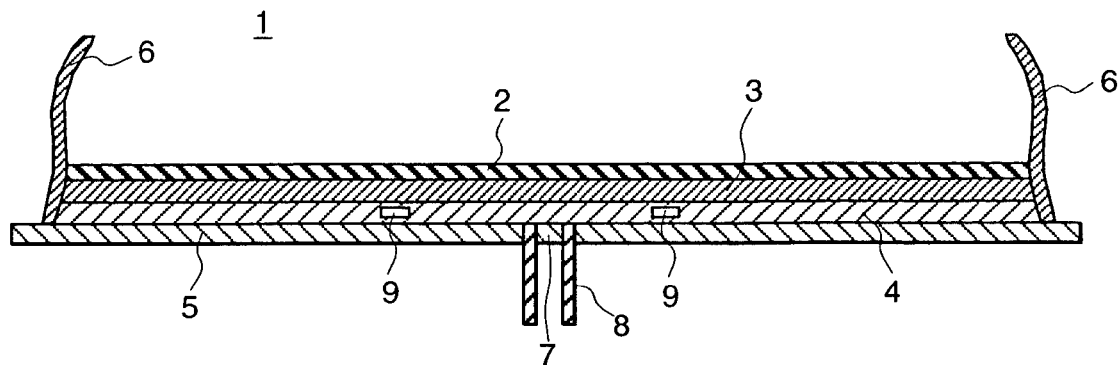

An embodiment of the present invention is shown in FIGS. 1 through 5. FIG. 1 is a schematic diagram of an automatic urine disposal device according to the present invention. FIG. 2 is a top view of the urine collecting pad, FIG. 3 is a bottom view of the urine collecting pad, FIG. 4 is an exploded perspective view of the urine collecting pad, and FIG. 5 is an enlarged cross-sectional view taken along A-A line in FIG. 2.

In FIGS. 1 through 5, a urine collecting pad 1 which absorbs urine discharged from a wearer's urinating part, not shown, is substantially rectangular, as shown in FIGS. 2 and 3, and its width at the middle portion in the longitudinal direction (direction of the wearer's front and rear) 2 is narrow so that it is shaped like an hourglass. The reason for this shape is to fit the wearer's crotch.

As shown in FIG. 4, the urine collecting pad 1 consists of a top sheet 2, hydrophilic sheet 3, urine absorbent sheet 4, outer sheet 5 and gathers 6. The top sheet 2 is liquid-permeable, breathable non-woven cloth. The hydrophilic sheet 3 is non-woven cloth made of polypropylene, polyethylene or rayon fibers, or made of composite fibers which compounds two or more fibers selected from the above mentioned fibers. The urine absorbent sheet 4 is made of molded material which is a compound of liquid-permeable non-woven cloth, flocculent pulp, and a polymer absorbent. The outer sheet 5 and gathers 6 are made of liquid-impermeable non-woven cloth or film.

The outer sheet 5 is a thin, liquid-impermeable sheet and is made of a polyethylene film, for example. The outer sheet 5 may be simply made of a liquid-impermeable member; however, desirably, an optimal member can be chosen by taking into account stuffiness which may result from the prolonged use. The outer surface of the outer sheet 5 is laminated with a soft and smooth surface material (not shown), such as a polypropylene non-woven cloth, to prevent the wearer from becoming uncomfortable. The inner surface of the outer sheet 5 has been treated with a water-repellent material.

Along the periphery of the outer sheet 5 in the longitudinal direction (direction of the wearer's front and rear) and the width direction, three-dimentional gathers 6 are created such that they are slanted inwardly along the periphery of the outer sheet 5 as shown in FIG. 5. These slantingly provided three-dimensional gathers 6 prevent leaks from the sides caused by the wearer's physical activity or change of posture. In addition, a through hole 7 through which a urine drainage tube 8 passes is created on the outer sheet 5.

A urine absorbent sheet 4 adheres to the top surface of the outer sheet 5 as shown in FIG. 5. Two urine sensors 9 are located on the urine absorbent sheet 4. The hydrophilic sheet 3 adheres to the surface of the urine absorbent sheet 4 so as to cover the entire surface of the urine absorbent sheet 4. The hydrophilic sheet 3 is almost the same shape as the urine absorbent sheet 4 as shown in FIG. 4.

The breathable, liquid-permeable top sheet 2 is disposed on the surface of the hydrophilic sheet 3. The top sheet 2 is made of a non-woven cloth so that rubbing between the wearer's skin and the fabric is minimized. In addition, a mesh sheet makes up a part of the surface of the non-woven cloth used as the top sheet 2 where it comes in contact with the wearer's urinating part and the surrounding skin. This is to increase the liquid-absorbent and sweat-absorbent capabilities so that urine can be quickly absorbed by the hydrophilic sheet 3 through small pores created in the mesh sheet. Because urine can be quickly absorbed by the urine absorbent sheet 4 via the hydrophilic sheet 3, the wearer has a minimal amount of discomfort due to moisture around the wearer's urinating part.

One end of the urine drainage tube 8 is connected to the urine drainage port 7 formed on the outer sheet 5. The other end of the urine drainage tube 8 is connected to a one-touch joint 11. The one-touch joint 11 is mounted to one end of the urine drainage tube 12, and this joint 11 connects the other end of the urine drainage tube 8 to the end of the urine drainage tube 12. The urine drainage tubes 8 and 12 are made of soft, flexible material such as soft resin, and the one-touch joint 11 is made of soft material.

A urine tank 15, which is elliptic-cylindrical and made of thick paper similar to paper used to make milk carton, has a bottom and an internal partition 16. A plurality of vacuum pores 17 are created on the partition 16. In addition, an arcuate protrusion 18 is formed on the outer circumference of the urine tank 15 to tightly engage with the lid container 20. The urine storage space 15a of the urine tank 15 contains superabsorbent resin 19 which turns into gel by absorbing urine. The superabsorbent resin 19 is particulate resin, and for example, cross-linked sodium polyacylate is used. The superabsorbent resin 19 constitutes a urine slosh inhibiting means which inhibits urine from sloshing in the urine tank 15.

The lid container 20 is made of paper and is elliptic-cylindrical to fit the urine tank 15, and a lid plate 21 which functions as a lid for the urine tank 15 is provided at the bottom of the lid container 20. When the lid container 20 caps the urine tank 15, the lid plate 21 seals the urine tank 15. The top opening of the lid container 20 is tightly covered with a deodorant filter material 22. The deodorant filter material 22 also functions as a lid of the lid container 20 and a ventilation pore 23 is created thereon. Furthermore, an arcuate recessed portion 28 is formed at the bottom of the lid container 20 to elastically engage with the arcuate protrusion 18 of the urine tank 15.

A vacuum pump 24 is located in the internal space created between the lid plate 21 of the lid container 20 and the deodorant filter material 22. The vacuum pump 24 is driven by a motor 25. The motor 25 uses a battery 26 as a driving power source, and is controlled by a control device installed in the control board 27. An alkaline cell or secondary cell is used as a battery 26. The vacuum pump 23 is small having a diameter of 30 mm and is at most 70 mm long. Voltage of the battery 26 is 5 to 9 V. A vacuum pump 24 is a rotary and displacement-type vacuum pump with rotating speed of maximum 5000 rpm.

This vacuum pump is designed based on the research result of the amount of urine discharged by an adult. That is, "Urinary bulletin" vol. 33, No. 4 (April, 1987) pages 521 to 526, which researched urine flow rate (amount of urine discharged per unit time) of each age group, was used as a reference. According to this document, maximum urine flow rate of a young adult (19 to 39 years old) is 28.2±4.6 ml per second and is more than any other age group. Accordingly, allowing for a margin of safety, maximum urine flow rate is accommodated at 40 ml per second which is at most 1.5 times as much as researched maximum urine flow rate. Therefore, when the vacuum pump suctions only urine without suctioning air, if the exhaust velocity of the vacuum pump is at least 40 ml/sec, urine can be properly suctioned without causing the urine collecting pad to overflow. In this embodiment, allowing for the maximum discharged urine flow rate to be two seconds, the volume of the buffer portion 2 in the urine collection pad is set to be 80 ml and the inner diameter of the urine discharge pore and the urine collecting tube 4 is set to be 3 to 4 mm.

The other end of the urine drainage tube 12 is located in the upper part of the urine storage space 15a of the urine tank 15 after passing through the lid container 20, lid plate 21, and the partition 16 of the urine tank 15. In addition, one end of the vacuum tube 30 which has the other end connected to the vacuum pump 24 is located in the space between the lid plate 21 and the partition 16. The vacuum tube 30 and the urine drainage tubes 8 and 12 are made of soft, flexible material.

The capacity of the urine tank 15 is about 500 ml which can store two separate urinations. This tank also comes in 200 ml or 1,000 ml which allows for the prolonged use at night.

A pair of urine sensors 9 which detect that urine has been discharged in the top sheet 2 electrically turns on by urination. It is electrically conductive and detects the wearer's urination by sensing the resistance value change. The urine detection signal detected by the urine sensors 9 is inputted via signal lines 31 and 32 into the control board 27 that controls the vacuum pump 24. The signal lines 31 and 32 are connected by a one-touch joint 33.

In this configuration, the urine collecting pad 1 is worn so that the top sheet 2 comes in contact with the urinating part of a wearer (not shown) in his/her underwear. The lid container 20 which encases the urine tank 15, vacuum pump 24, and the motor 25 can be carried by the wearer or can be placed on or under the bed on which the wearer lies.

When the wearer urinates in this situation, urine discharged in the urine collecting pad 1 is absorbed by the top sheet (non-woven cloth) 2, and then saturates the hydrophilic sheet 3. The hydrophilic sheet 3 widely diffuses urine to saturate its entire surface by surface tension. The interfiber spaces of the hydrophilic sheet 3 are saturated with urine, and the hydrophilic sheet 3 becomes non-breathable. When urine is absorbed by the urine absorbent sheet 4 via the hydrophilic sheet 3, the urine sensor 9 is electrically turned on, and a urine detection signal is inputted into the control board 27. The control device installed in the control board 27 activates the motor 25 to drive the vacuum pump 24.

When air in the urine tank 15 has been vacuumed by the vacuum pump 24, air pressure in the urine storage space 15a decreases, creating negative pressure in a urine drainage port 7 of the outer sheet 5. The hydrophilic sheet 3 has been non-breathable due to urination, and the outer sheet 5 is non-breathable, and therefore, the urine absorbent sheet 4 is kept airtight.

When pressure in the urine drainage port 7 becomes negative, urine absorbed in the urine absorbent sheet 4 is quickly drawn into the urine drainage tube 8 by means of a vacuum force due to negative pressure. Urine drawn into the urine drainage tube 8 is further drawn into a urine storage space 15a of the urine tank 15 by the negative pressure via the urine drainage tube 12 and stored in the tank.

Moreover, the inner surface of the outer sheet 5 has been treated with a water-repellent material. Urine absorbed in the urine absorbent sheet 4 is quickly drawn into the urine drainage port 7.

Urine drawn into the urine storage space 15a of the urine tank 15 reacts with particulate superabsorbent resin 19 and turns into gel. Once urine has turned into gel, it is possible to inhibit urine from sloshing in the urine tank 15. Therefore, a desirable automatic urine disposal device can be configured which does not leak urine during the time the device is being carried.

When the wearer has finished urinating and the urine sensor 9 has stopped sending the urine detection signal, the control device installed on the control board 27 stops the operation of the motor 25 thereby stopping the vacuum pump 24. If the capacity of the urine tank 15 is large enough to store the contents of two separate urinations, the subsequent urination will be handled in the same way.

The urine tank 15 can be removed by disconnecting the urine drainage tubes 8 and 12 by unlocking the one-touch joint 11 as well as by disconnecting the signal lines 31 and 32 by unlocking the one-touch joint 33. After that, the urine tank 15 which stores urine is removed from the lid container 20 and the urine tank 15 will be discarded. The urine tank 15 is made of paper and can be disposed of as a combustible material.

Moreover, after the wearer has worn the urine collecting pad 1 for a day or when it became dirty due to defecation, the used urine collecting pad 1 is discarded by disconnecting the urine drainage tube 8 from the urine sensors 9 by unlocking the joints 11 and 33, and the wearer wears a new urine collecting pad 1.

Thus, urine discharged by a wearer is disposed of. A urine collecting pad 1 according to the present invention is designed such that the urine absorbent sheet 4 is kept airtight by the outer sheet 5 and the hydrophilic sheet 3 upon urination. Accordingly, the percentage of urine collection from the urine collecting pad 1 by the operation of the vacuum pump 24 increases and the amount of urine which remains in the urine collecting pad is reduced. With the increase in the percentage of urine collection, a small capacity vacuum pump 24 with a low vacuum force can drain urine. Therefore, it is possible to drain urine from the urine collecting pad 1 without discomfort to the wearer, and the device can be compact and lightweight.

Since the device can be compact and lightweight, if it is used as a portable automatic urine disposal device, it will be most efficient. Furthermore, because the device is compact and lightweight and the vacuum pump does not unnecessarily suction air, noise is minimal and urine can be quietly drained without bothering other patients in the room at night.

Figure 6:
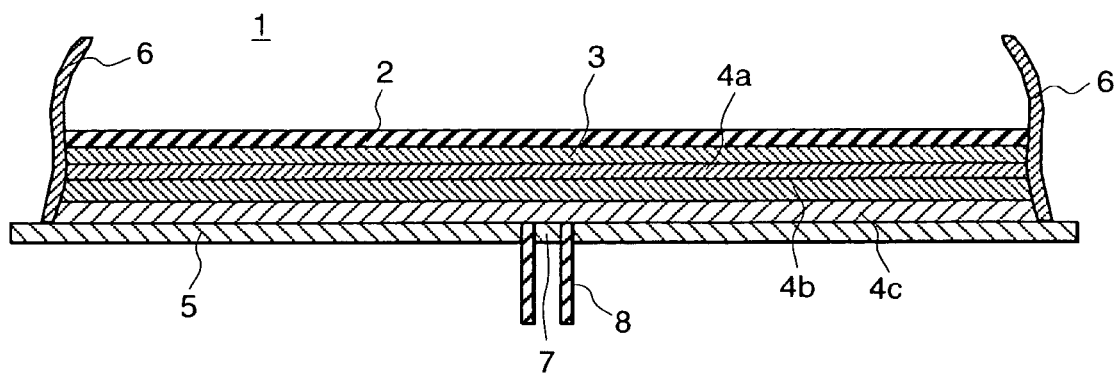
FIG. 6 is a cross-sectional view, corresponding to FIG. 5, of another embodiment of the urine collecting pad.

FIG. 6 shows another example of the urine collecting pad 1. The urine collecting pad 1 shown in FIG. 6 is different from the urine collecting pad shown in the aforementioned embodiment because in the urine collecting pad 1 shown in FIG. 6, the urine absorbent sheet 4 is made up of laminated multiple layers (3 layers) 4a, 4b, and 4c, and each layer of the urine absorbent sheet 4a, 4b, 4c has different water-absorbing properties (water-retentive capability) so that the water-absorbing property of layer 4a is smaller than that of layer 4b, and that of layer 4b is smaller than that of layer 4c which is the bottom layer.

The different water-absorbing properties of the urine absorbent sheets 4a, 4b and 4c can be achieved by providing different density and wettability for a porous, fibriform, skeletal material. By thus providing urine absorbent sheets 4a, 4b and 4c with different water-absorbing properties, urine is easily collected in the bottom layer of the urine absorbent sheet 3c which has the highest water-absorbing property. Since urine gathers in the bottom layer of the urine absorbent sheet 4c which abuts on the outer sheet 5 on which a urine drainage port 7 is created, urine can be efficiently absorbed.

Furthermore, by making two layers of the urine absorbent sheets 4a and 4b by using material that has fibers arranged vertically (in the thickness direction), it is possible to collect urine in the urine absorbent sheet 4c without urine seeping in the transverse direction.

Moreover, by configuring the hydrophilic sheet 3 with multiple layers instead of using the urine absorbent sheet 4 and providing those layers of hydrophilic sheet with different water-absorbing properties (water-retentive capability), the same effect as the above can be achieved.

Figure 7:
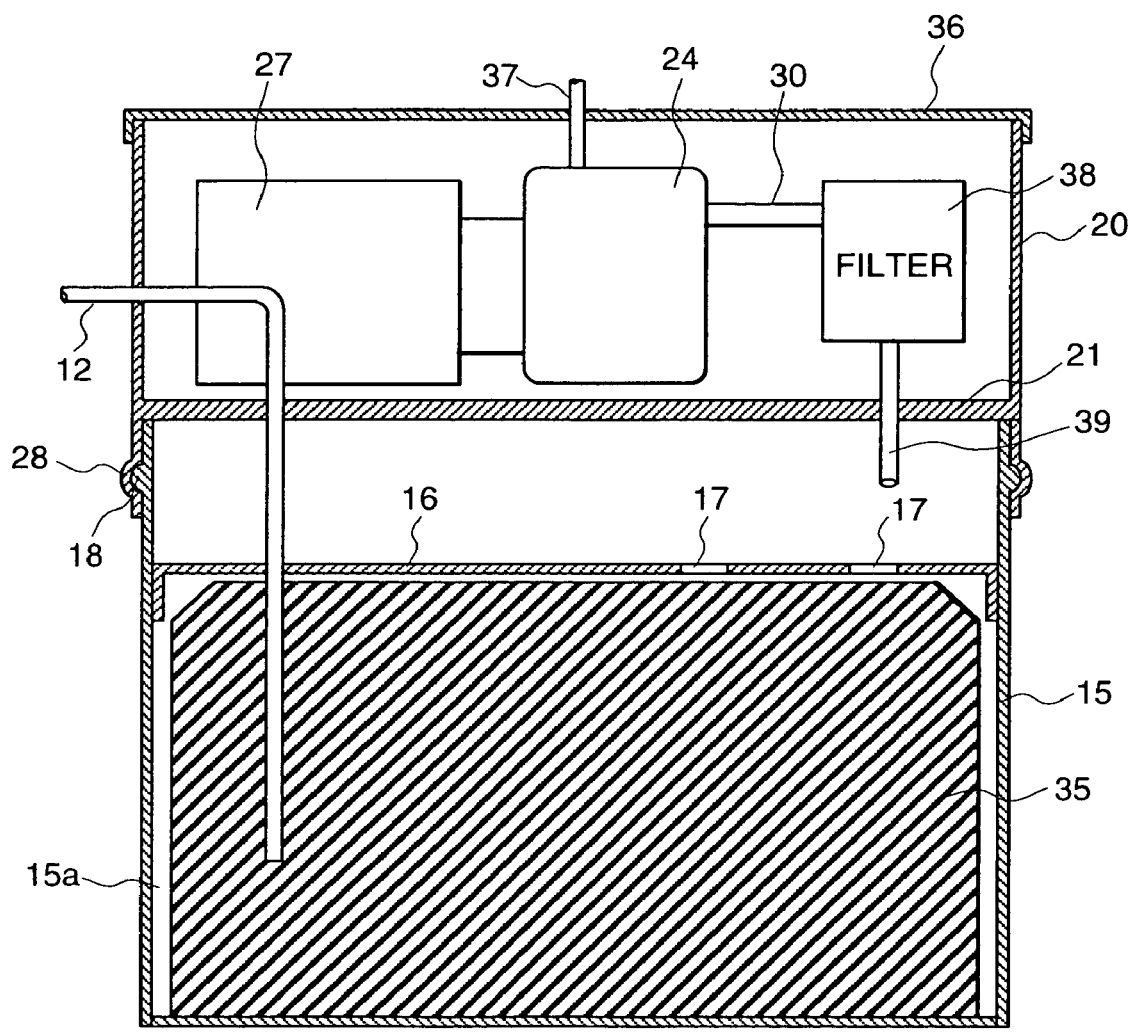
FIG. 7 is an elevation partly in section of a urine tank installed in the automatic urine disposal device shown in FIG. 1.

FIG. 7 shows another example of the urine tank (including a lid container). The urine tank 15 shown in FIG. 7 is different from the urine tank in the aforementioned embodiment shown in FIG. 1 because both the urine tank 15 shown in FIG. 7 and the lid container 20 are designed to be rectangular, and a porous urine absorbent material 35 is provided as a urine slosh inhibiting means. Sponge-like material or pumice is used as a porous urine absorbent material 35.

In FIG. 7, a lid plate 36 is provided in the lid container 20 and a deodorant filter 38 is also disposed in the lid container 20, and air is vacuumed from the urine tank 15 via a vacuum tube 39. The vacuum pump 24 discharges air via a discharge tube 37. The motor 25 is located behind the vacuum pump 24 and is not shown.

This configuration also inhibits urine drawn into the urine storage space 15a of the urine tank 15 from sloshing in the urine tank 15 because urine is absorbed by the porous urine absorbent material 35.

As stated above, the present invention increases the percentage of urine collection from the urine collecting pad 1 and reduces the amount of urine which remains in the urine collecting pad. With the increase in the percentage of urine collection, a small capacity vacuum pump with a low vacuum force can drain urine. Therefore, it is possible to drain urine from the urine collecting pad 1 without discomfort to the wearer, and the device can be compact and lightweight.

Since the device can be compact and lightweight, if it is used as a portable automatic urine disposal device, it will be most efficient. Furthermore, because the device is compact and lightweight and the vacuum pump does not unnecessarily suction air, noise is minimal and urine can be quietly drained without bothering other patients in the room at night.

Moreover, in the aforementioned embodiment, the urine tank is made of paper and can be disposed of as a combustible material. As a result, an environment-friendly urine disposal device can be obtained.

Moreover, in the aforementioned embodiment, the hydrophilic sheet becomes non-breathable when it absorbs urine; however, it is obvious that the hydrophilic sheet can become hard-breathable allowing for a little breathing.

Furthermore, it is obvious that the urine tank and the lid container can be made of plastic instead of paper, and the urine slosh inhibiting means can solidify urine. Moreover, an IC chip can be used as a urine sensor to wirelessly send a urine detection signal.

Because the present invention increases the percentage of urine collection from the urine collecting pad and reduces the amount of urine which remains in the urine collecting pad, a small capacity vacuum pump with a low vacuum force can drain urine. Therefore, it is possible to drain urine from the urine collecting pad without discomfort to the wearer, and the device can be compact and lightweight.

Since the device can be compact and lightweight, if it is used as a portable automatic urine disposal device, it will be most efficient. Furthermore, because the device is compact and lightweight and the vacuum pump does not unnecessarily absorb air, noise is minimal and urine can be quietly drained without bothering other patients in the room at night.

The preferred embodiments described herein are illustrative and not restrictive, the scope of the invention being indicated by the appended claims and all variations which come within the meaning of the claims are intended to be embraced therein.

What is claimed is:

1. An automatic urine disposal device comprising:
    a top sheet made of a breathable and liquid permeable non-woven cloth, wherein said top sheet has a mesh structure at a surface thereof to which the wearer's skin comes in contact;
    a urine absorbent sheet made of polymeric material;
    a hydrophilic sheet disposed between said top sheet and said urine absorbent sheet, said hydrophilic sheet comprising a non-woven cloth made of polypropylene, polyethylene or rayon fibers or made of compound fibers of a composite of two or more fibers selected from the group consisting of polypropylene, polyethylene and rayon fibers;
    an outer sheet formed with a thin sheet made of one liquid-impermeable material selected from the group consisting of a non-woven cloth and a film, wherein said outer sheet is given a water-repellent surface treatment on its inner surface and wherein said outer sheet has said urine absorbent sheet being adhered thereon;
    gathers slanted inwardly provided on said outer sheet along its contours in longitudinal direction and width direction;
    a urine drainage tube made of soft and flexible material for directing urine in said urine absorbent sheet to a sealed urine tank through a urine drainage port to which a one-touch joint made of soft material is connected;
    a urine sensor for detecting urine discharge in said top sheet; and
    a vacuum pump to lower the pressure inside said urine tank; and said hydrophilic shoot, and
    a control device operably connected to said urine sensor for starting said vacuum pump on urine discharge in said top sheet according to a signal from said urine sensor and for stopping said vacuum pump on ending of urination.

2. The automatic urine disposal device according to claim 1, wherein said hydrophilic sheet is disposed such that it covers said urine absorbent sheet.

3. A automatic urine disposal device according to claim 2, wherein
    said hydrophilic sheet becomes non-breathable by being saturated with urine which has flowed in from said top sheet.

4. The automatic urine disposal device according to claim 2, wherein
    said outer sheet is non-breathable, and
    said urine absorbent sheet is disposed such that its backside adheres to said outer sheet and is made up of multiple layers.

5. The automatic urine disposal device according to claim 1, further comprising a urine tank.

6. The automatic urine disposal device according to claim 5, wherein
    said hydrophilic sheet becomes non-breathable when urine diffuses and saturates said hydrophilic sheet,
    said urine tank has a lid to seal the tank, and
    there is provided a urine slosh inhibiting means for inhibiting urine which has flowed into said urine tank from sloshing.

7. The automatic urine disposal device according to claim 6, wherein
    a joint which connects said lid to said urine drainage tube is provided so that urine can be directed to said urine drainage tube through said lid, and
    said urine absorbent sheet is made up of multiple layers.

8. The automatic urine disposal device according to claim 7, wherein said urine absorbent sheet is made up of multiple layers in which the water-absorbing property becomes higher as the layer becomes further from said top sheet.

9. The automatic urine disposal device according to claim 5;
    further comprising a battery for driving said vacuum pump and
    a container which integrates said vacuum pump, urine tank, and battery into one body, said container having a partition means which separates the urine tank, vacuum pump, and battery from one another.

10. A urine receptacle according to claim 1, wherein said hydrophilic sheet becomes non-breathable by being saturated with urine which has flowed in from said top sheet.

11. The urine receptacle according to claim 1, wherein
said outer sheet is non-breathable, and
said urine absorbent sheet is disposed such that its backside adheres to said outer sheet and is made up of multiple layers.

12. The automatic urine disposal device according to claim 1, wherein
said urine absorbent sheet has a buffer portion made of porous fibriform skeletal material, and
the fibriform skeletal material is selected from the group consisting of non-woven cloth, foam structural material, PE mesh sheet, sodium carboxymethyl cellulose, superabsorbent resin, and flap-type wood pulp which dispersively contains such materials.

13. The automatic urine disposal device according to claim 1, wherein
said vacuum pump is a rotary, displacement-type vacuum pump with rotating speed of maximum 5,000 rpm, and the vacuum pumping speed is 40 ml/sec or less.

14. The automatic urine disposal device according to claim 1, wherein
said urine absorbent sheet has a buffer portion which encases a material selected from the group consisting of superabsorbent resin, sponge-like material, and porous material.

15. The automatic urine disposal device according to claim 1, wherein
the inner surface of said urine tank is water repellent,
a joint is provided to connect the urine tank to the urine drainage tube, and
the urine tank is replaceable by disconnecting the joint.

* * * * *